United States Patent [19]
Rhodes

[11] Patent Number: 5,708,275
[45] Date of Patent: Jan. 13, 1998

[54] PH MEASUREMENT UTILIZING A LIGHT SOURCE

[75] Inventor: Michael L. Rhodes, Richfield, Minn.

[73] Assignee: Honeywell Inc., Minneapolis, Minn.

[21] Appl. No.: 660,140

[22] Filed: Jun. 7, 1996

[51] Int. Cl.$^6$ .................................................. G01N 21/64
[52] U.S. Cl. .............................. 250/461.1; 250/252.1 A; 162/49
[58] Field of Search ..................... 250/461.1, 459.1, 250/252.1 A; 356/318, 317; 162/49

[56] References Cited

U.S. PATENT DOCUMENTS

| | | | |
|---|---|---|---|
| 5,220,172 | 6/1993 | Berthold et al. | 250/461.1 |
| 5,456,252 | 10/1995 | Vari et al. | |
| 5,486,915 | 1/1996 | Jeffers et al. | 250/461.1 |

Primary Examiner—David P. Porta
Assistant Examiner—Richard Havig
Attorney, Agent, or Firm—Charles J. Ungemach; John G. Shudy, Jr.

[57] ABSTRACT

The pH of a material containing lignin is determined by directing an ultraviolet light at the material. One of the characteristics of lignin is giving off a fluorescence in response to an ultraviolet light. A monochrometer is used to observe the fluorescence and produces a signal of the intensity of the fluorescent light at varying wavelengths. This signal is displayed on a display means such as a computer screen. Calibration occurs before the pH measurement of the material occurs. The calibration data along with information from the signal is used to calculate the pH of the material. No contact with the material is required in determining the pH of the material.

5 Claims, 3 Drawing Sheets

PH MEASUREMENT UTILIZING A LIGHT SOURCE

BACKGROUND OF THE INVENTION

Determining the pH of a material is important in the paper and pulp making process. In paper making, acid content degrades the quality of the paper. The higher the acid content, the quicker the paper fades and curls. If the pH is known while making paper, the paper could be made with a lower acid content so a higher quality paper is produced. In pulping, it is desirable to have a high bleaching effect. The rate of bleaching is dependent on the pH balance so determining the pH is very important in the pulping process as well.

Currently, two principal methods exist in determining the pH of a material. One method is colorimetrically and the other method is electrometrically. The first method measures the pH of a material based on its color change when it is exposed to an organic dye. This method is commonly performed by litmus paper, but other indicators and test papers are also available. The problem with this method is that it exposes the material to the organic dye such that the material is contaminated due to the contact. Another problem with this method is that it has a very narrow range of pH values it can determine.

The second method uses electrodes and a pH meter. The problem with this method is that it requires contact with the material and is a very slow process. The process requires the substance to exist in a chemical environment for an unacceptably long time. A glass electrode is used to measure the pH, but the chemical environment perpetually confuses the measuring bulb of the electrode and degrades the signal and perhaps even inactivates the electrode's measuring capability. The electrode has to be cleaned periodically in order for an accurate measurement to be determined. The electrode is very fragile, and as stated before, this is a very slow process. It would be beneficial for the pulp and paper making industry to have a faster noncontact means of determining the pH of a material.

SUMMARY OF THE INVENTION

The present invention provides means to determine the pH of a material without contacting it. The present invention also provides a quick reading of pH. The present invention includes an ultraviolet light source, a monochrometer, and means to display a light signal. The light source will shine an ultraviolet light beam on the material for which the pH is to be determined. The material will emit a fluorescence as a result. The monochrometer will be used to absorb the fluorescence and determine the intensity at varying wavelengths. A signal of the intensity of the fluorescent light at varying wavelengths can then be produced on a display means. The pH can be determined by using information from the graph in combination with a predetermined equation.

DETAILED DESCRIPTION

Figure 1:
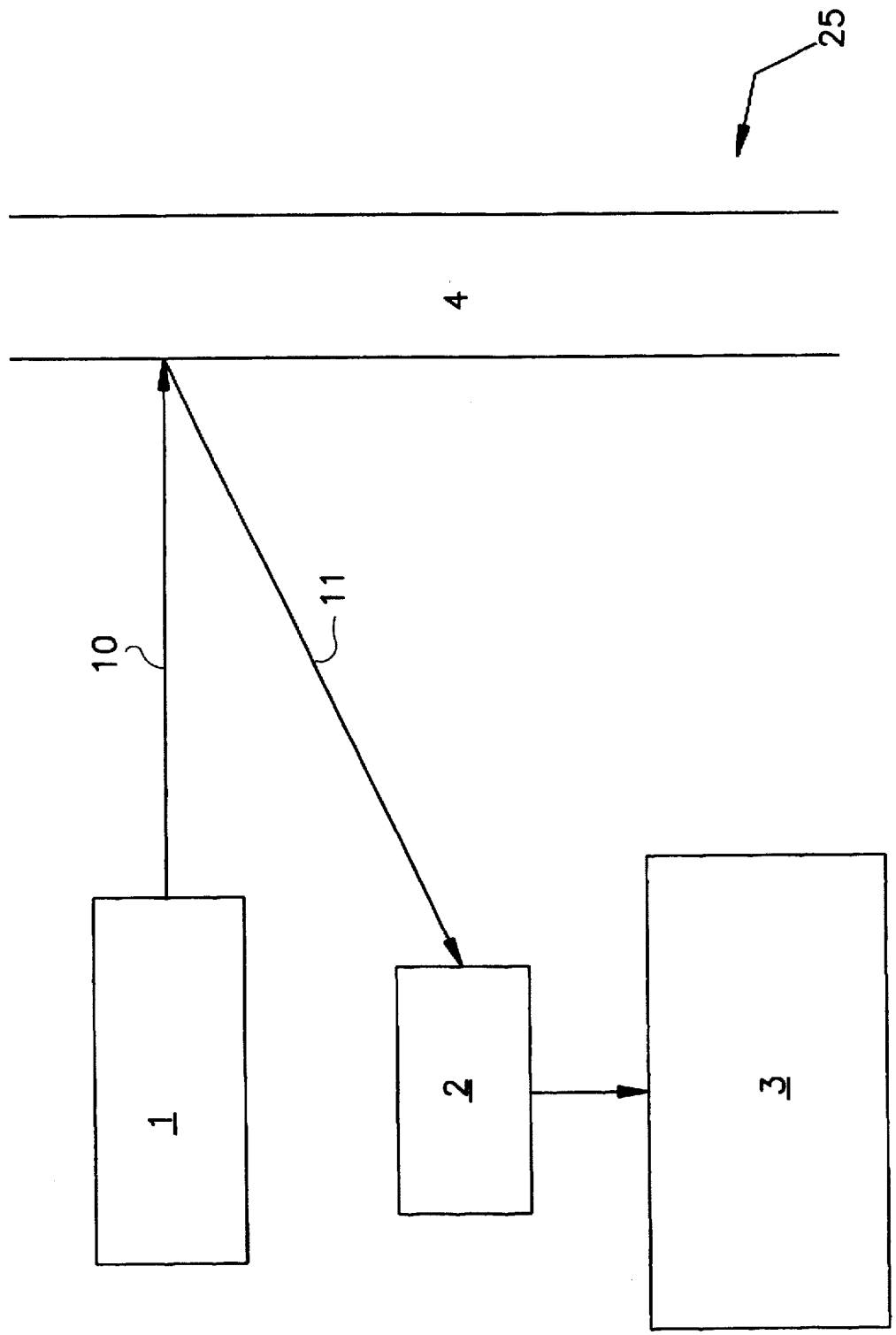
FIG. 1 is a block diagram of means of determining pH of a material in accord with a preferred embodiment of this invention.

FIG. 1 shows the present invention in a block diagram 25. The present invention generally includes a light source 1, a monochrometer 2, and a display means 3, such as a computer monitor, that is capable of displaying representations of light signal values The present invention is used to determine the pH of a material 4, preferably such as pulp or paper. Materials such as those stated contain a substance called lignin. Lignin is the "glue" that holds the fibers together in wood. There are many different types of lignin and one of the characteristics of all of them is that lignin gives off a fluorescence in response to ultraviolet light. It has been well known in the past that lignin actively fluoresces in response to ultraviolet radiation. This characteristic of lignin has been used before, but only to measure the lignin content of pulp and paper in the paper making process.

Fluorescence is the absorbing of light and re-emission of light at a different, longer wavelength. In lignin, the wavelength of the re-emitted light depends on the Hydrogen ion concentration of the material. Therefore, the pH of the material (which is directly related to free Hydrogen ions) can be determined. However, the lignin only emits fluorescent light in response to ultraviolet light. Therefore, in the preferred embodiment the light source 1 is an ultraviolet light source. Many ultraviolet light sources are available and well known that can be used in the present invention. Some common examples are lasers or Xenon flash lamps although other ultraviolet light sources can also be used.

FIG. 1 shows a light beam 10 emitted from the light source and a fluorescent light 11 emitted once the light beam 10 has been shined on the material 4. The distance from the light source 1 to the material 4 is not critical, but the closer the light source 1, the higher the relative intensity of the light beam 10. As a result, the intensity of the fluorescence 11 will be higher and it will be easier to measure. The angle that the light beam 10 from the light source 1 is pointed at the material 4 is not critical either since the monochrometer 2 will be directed at the point the light beam 10 from the light source 1 hits the material 4.

The monochrometer 2 absorbs the fluorescent light 11 and communicates the intensity of the fluorescent light at particular wavelengths across the fluorescent spectrum to a display means 3. The monochrometer 2 is preferably connected to the display means 3 by a simple electrical connection. In monochrometers, a control means exists that changes the wavelength so that different intensities of a light beam are absorbed. Monochrometers are well known and methods and cables for connection to computers and computer displays are also well known. Many companies manufacture and sell monochrometers such as Monolight Instruments in Godlaming, United Kingdom, Perkin-Elmer Corporation in Norwalk, Conn. and Ocean Optics in Dunedin, Fla. There are basically three main types of monochrometers which are the Ebert mount, Littron mount, and the Straight prism monochrometer. The Ebert mount monochrometer is preferred, because it is the most accurate. It is well known that monochrometers measure intensity of light in relation to a selected wavelength of the light. This occurs very quickly at about 0.015 seconds in many modern monochrometers. The display means 3 then displays a signal 8 of the light beam 10 as the intensity of the light beam in relation to the wavelength of the light beam.

Figure 2:
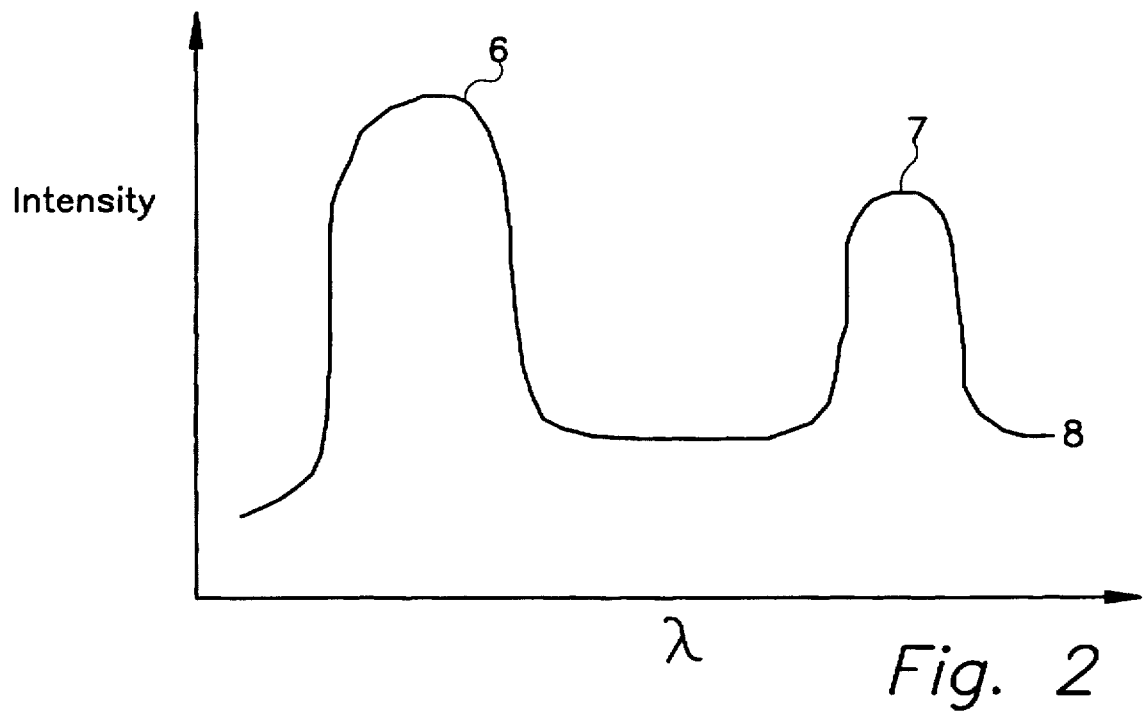
FIG. 2 is a graph of a light signal that is used to assist in determining the pH of a material in accord with a preferred embodiment of the invention.

FIG. 2 shows the signal 8 of the light beam as it may be displayed on the display means 3. Two peaks exist. One peak (either peak 6 or peak 7) indicates the presence and amount of the lignin with a hydrogen ion attached to it (HL) or otherwise called lignin acid. The other peak 6 or 7 represents just the lignin (L) itself, without the hydrogen ion attached to it, as it exists as a base. An equation is used to determine the pH:

$$pK_a - \log(HL/L) = pH.$$  Eq. 1

$pK_a$=Log of the dissociation constant.

The dissociation constant is the value representing the equilibrium between the undissociated and dissociated forms of a molecule. The peaks 6 and 7, however, are indeterminate as to which peak belongs to the HL and which to the L. Two calibration methods will resolve this problem. The pH of the material 4 is then determined based on the information the signal 8 provides along with the calibration information.

Figure 3:
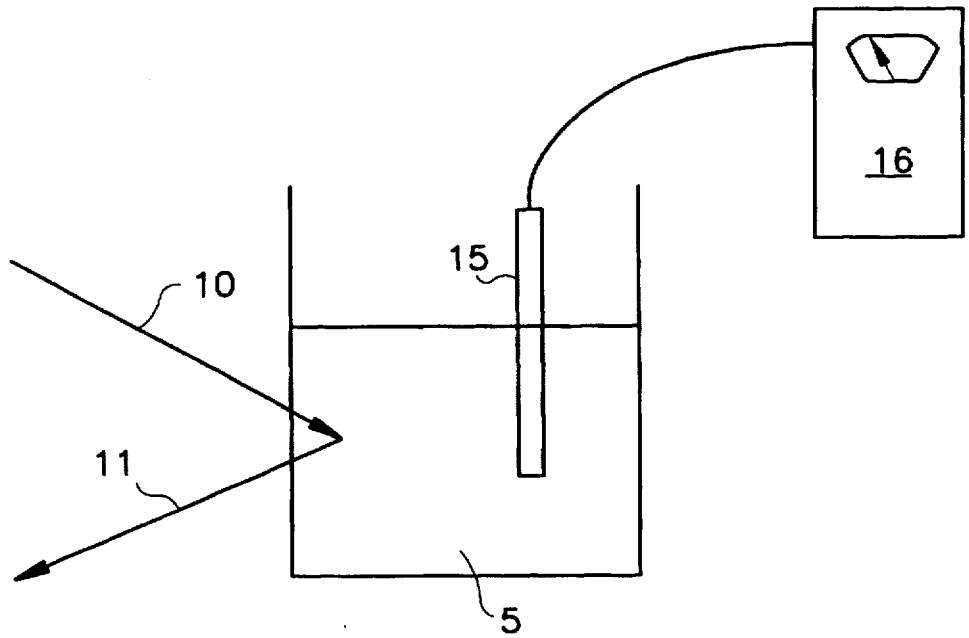
FIG. 3 shows a means of calibration for use with or in this invention.

Preferably, calibration should be performed before the pH determining process. The process for calibration can be described with reference to FIG. 3. A small sample of the material is taken and ground into a pulp. It is then placed in a container containing a chemical solution of a known pH. These chemical solutions in this area of technology are commonly called buffer solutions. Some examples of buffer solutions are disodium hydrogen phosphate which has a pH of approximately 6.9, borax solution which has a pH of 9.2 and potassium hydrogen phthalate which has a pH of 4. An electrode 15 is placed in the container touching the material and buffer solution 5. A pH meter 16 is connected to the electrode 15 to verify the pH of the solution and the sample of the material 5. The electrode 15 and pH meter 16 are not necessary since the solutions already have a known pH, but are used merely for redundant verification in the preferred embodiment.

The process is then performed as described before. The ultraviolet light source 1 shines a beam at the material in the buffer solution 5 and a light signal 8 of the intensity of the fluorescent light 11 at varying wavelengths may be represented in a display on a display means 3. This signal 8 is recorded for the level of pH of the particular buffer solution. For example, the sample of the material is ground and placed in a buffer solution of pH that is 4 such as potassium hydrogen phthalate. The ultraviolet light 10 is shined on the sample 5 and the logarithm of the ratio of HL to L (log HL/L) is recorded for the pH of the buffer which in this case is 4. Again, the problem exists in that it is unknown as to which peak represents the concentration of HL., and which peak represents L. Two possible calibration techniques can be implemented to solve this problem. The calibration techniques are: a) creation of a calibration graph and b) two point calibration.

Figure 4:
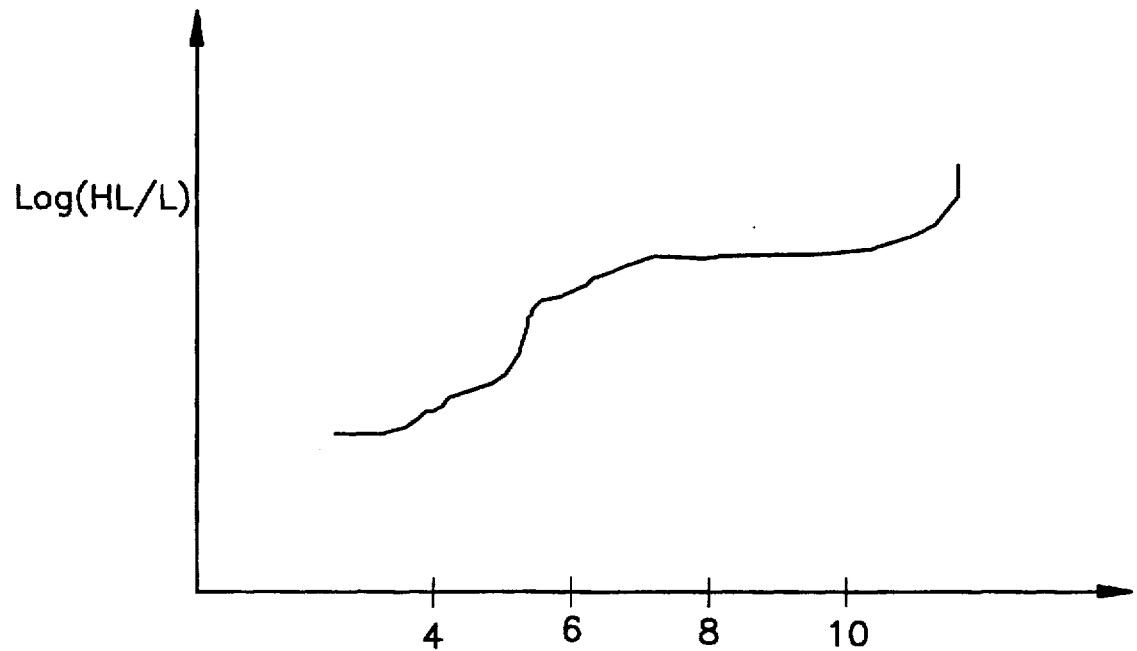
FIG. 4 shows a calibration graph.

FIG. 4 displays a calibration graph. In creating a calibration graph, the log(HL/L) is determined and graphed in relation to the pH of the buffer solution for varying pH's so that a calibration graph is created. For example, the differing pH levels could be at 6, 8, 10, etc. Later, when the pH of a material is desired, the log(HL/L) of the signal 8 on the display means 3 is taken and matched with where the log(HL/L) value is on the calibration graph. The pH is then determined by looking on the x-axis to find the pH value associated with that point on the calibration graph. Sometimes, the actual log(HL/L) value may not be precisely on the calibration graph, but the point on the graph that it is closest to is used to determine the pH. The problem still exists in that the peaks are unknown. This will not matter in this calibration method, because the value of the logarithm of the ratio will remain the same and the only difference will be a change in the sign of the value. This is one method of calibration that can be used to determine pH.

Figure 5:
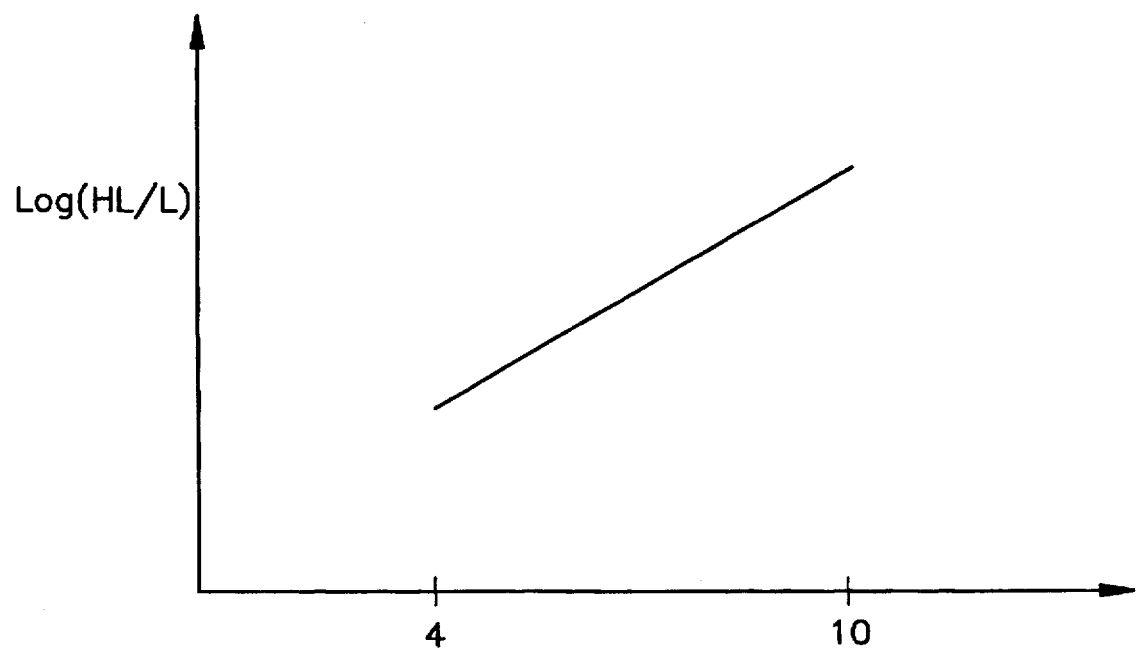
FIG. 5 shows a two point calibration graph.

The other calibration method is called a two point calibration which can be performed instead of creating a calibration graph. The two point calibration only requires measuring the log(HL/L) at two different pH levels. A line is then drawn connecting the two points. If the slope is positive, then the base, L, is the first peak on the display means 3 and the acid, HL, is the second peak. On the other hand, if the slope is negative, then the acid is the first peak and the base is the second peak. FIG. 5 shows a two point calibration graph with a positive slope. The dissociation constant differs from material to material. Once it is determined which peak belongs to the base and which peak belongs to the acid, the constant can be determined based on the equation used to determine pH (For example, if the pH of the buffer solution is 4 and the ratio is 1, putting these values into Eq. 1 would result in the constant being $10^{4+\log}$).

Later, when the pH of a material is desired, it is known, from the calibration, which peak is the base and which is the acid. Also, the dissociation constant is known as well. The pH can be easily calculated using Eq. 1.

What is claimed is:

1. A method for determining the pH of a lignin containing substance comprising:

a) directing an ultraviolet light at the substance;

b) measuring the intensity of the fluorescence of the substance at particular wavelengths; and c) determining the pH of the substance with information from a graph.

2. The method of claim 1 further including a step of calibrating a known value of pH prior to step a).

3. The step of calibrating of claim 2 wherein the step comprises:

a) taking a sample of the substance;

b) placing the sample in a solution of a known pH;

c) directing ultraviolet light at the sample in the solution of a known pH;

d) measuring the intensity of the fluorescence of the sample in the solution of a known pH at particular wavelengths;

e) recording information obtained from the intensity measurement;

f) repeating the steps from step b) for different pH values; and g) using information from the intensity measurement for different pH values to create a graph.

4. The process for calibration of claim 3 wherein steps b) through d) are performed a plurality of times.

5. A method for determining the pH of a lignin containing material comprising:

a) directing an ultraviolet beam at the material;

b) measuring the intensity at particular wavelengths of a fluorescent light beam emitted from the material after the ultraviolet light beam has hit the material; and c) determining pH based on the measured intensity at said particular wavelengths.

* * * * *